US00PP29129P2

(12) United States Plant Patent
Sheehan

(10) Patent No.: US PP29,129 P2
(45) Date of Patent: Mar. 20, 2018

(54) GRAPEVINE PLANT NAMED 'SHEEGENE 27'

(50) Latin Name: *Vitis vinifera*
Varietal Denomination: Sheegene 27

(71) Applicant: Sheehan Genetics, LLC, Fresno, CA (US)

(72) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 15/530,003

(22) Filed: Nov. 16, 2016

(51) Int. Cl.
*A01H 5/08* (2006.01)

(52) U.S. Cl.
USPC ..... Plt./205

(58) Field of Classification Search
USPC ..... Plt./205
See application file for complete search history.

(56) References Cited

U.S. PATENT DOCUMENTS

| | | | |
|---|---|---|---|
| PP4,787 | P | 11/1981 | Olmo |
| PP17,211 | P2 | 11/2006 | Gargiulo |
| PP17,504 | P3 | 3/2007 | Maranto |
| PP17,875 | P3 | 7/2007 | Gargiulo |
| PP18,226 | P3 | 11/2007 | Gargiulo |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,599 | P2 | 12/2008 | Maranto |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,075 | P2 | 6/2010 | Maranto |
| PP21,316 | P3 | 9/2010 | Sheehan |
| PP23,125 | P2 | 10/2012 | Sheehan |
| PP23,478 | P3 | 3/2013 | Chimenti |
| PP23,837 | P3 | 8/2013 | Sheehan |
| PP25,095 | P3 | 11/2014 | Sheehan |
| PP25,131 | P3 | 12/2014 | Sheehan |
| PP26,179 | P3 | 12/2015 | Sheehan |
| PP26,300 | P3 | 1/2016 | Lombard |
| 2008/0201809 | P1 | 8/2008 | Sheehan |
| 2013/0276181 | P1 | 10/2013 | Sheehan |
| 2016/0044845 | P1 | 2/2016 | Sheehan |

*Primary Examiner* — Annette H Para
(74) *Attorney, Agent, or Firm* — Dentons US LLP

(57) ABSTRACT

A new and distinct grapevine plant named 'Sheegene 27' is described herein. The claimed variety was developed as a table grape and for raisin production, having uniform medium-sized, green, globose, seedless fruit weighing approximately 3 g each and having a crisp texture and neutral flavor. Harvest is in late-July to mid-August.

1 Drawing Sheet

Latin name of the genus and species of the plant claimed: *Vitis vinifera.*

Variety denomination: 'Sheegene 27'.

BACKGROUND OF THE INVENTION

The present invention relates to a new and distinct variety of grapevine named 'Sheegene 27'. 'Sheegene 27' produces medium-sized, green-yellow, seedless grapes on bunches for use as a table grape and in raisin production. The variety originated from a cross of 'Very Early Flame' (also known as 'VEF') as the pollen parent and 'Red Globe' (U.S. Plant Pat. No. 4,787) as the seed parent. 'Sheegene 27' was first asexually propagated in the San Joaquin Valley of California. All characteristics and distinctions remain true to form and are established and transmitted through succeeding propagations.

SUMMARY OF THE INVENTION

The present invention relates to a new and distinct grapevine plant called 'Sheegene 27'. 'Sheegene 27' produces medium-sized berries averaging 3 g per berry. The berries are harvested in late-July to mid-August. Comparison can be made to 'Thompson Seedless' (unpatented), which is also a green, seedless grape grown for both table grape and raisin production. 'Sheegene 27' matures 10 days earlier than Thompsons Seedless, and about the same time as Selma Pete, a grape cultivar grown for raisin cultivation. Berries of 'Sheegene 27' are globose, while both Thompson Seedless and Selma Pete are ellipsoid pointed. Thompson Seedless and Selma Pete berries weigh approximately 2 grams, while 'Sheegene 27' berries are larger, weighing around 3 grams.

BRIEF DESCRIPTION OF THE DRAWINGS

'Sheegene 27' is illustrated by the accompanying photograph, taken of a 5-year-old vine, which shows the plant's vines, foliage, and fruit. The colors shown are as true as can be reasonably obtained by conventional photographic procedures.

FIG. 1—Shows the typical morphology of stems, leaves, grapes, and tendrils of 'Sheegene 27'.

DETAILED BOTANICAL DESCRIPTION

Phenotypic Description of *Vitis vinifera* 'Sheegene 27', obtained from 5-year-old plants growing in Delano, Calif.

The colors (except those in common terms) are described using the Munsell Color Charts for Plant Tissue by Munsell Color, 617 Little Britain Rd., New Windsor, N.Y. 12553-6148, 1977 revision.

Classification:

*Family*.—Vitaceae.

*Botanical name*.—*Vitis vinifera*.

Plant:

*Plant habit and growth*.—Moderate to high vigor, trailing with light secondary shoot development.

*Size*.—Age at maturity: 3 to 4 years. Height (at maturity): Cordon: 120 cm; Canopy: 220 cm. Width (at maturity): 240 cm. Vigor: Medium high. Productivity: High.

Trunk:

*Diameter*.—6.4 cm measured 45 cm from floor.

*Surface texture*.—Coarse, rough.

*Color*.—Exposed surface=(5 YR 5/2); interior surface=(2.5 YR 5/4).

Canes (quadrilateral spurs):

*Size*.—Diameter: 1 cm (basilar measurement). Length: 140 cm.

*Surface texture* (*mature cane*).—Smooth.

*Surface texture* (*immature cane*).—Smooth.

*Form* (*woody shoot cross section form*).—Pith in center with diaphragm at nodes.

*Color* (*mature*).—5 YR 6/6 at 20 weeks.

*Color* (*immature*).—2.5 GY 8/8 at 6 weeks; anthocyanin pigment (5R 5/8).

*Internode length* (*upper mature sun cane*).—10.4 cm.

Time of bud burst.—Budbreak (50% buds opened) occurs the end of April.

Tendrils:

*Form*.—Mostly bifid, some trifid.

*Size*.—Medium.

*Length*.—18 cm on average.

*Diameter*.—2.5 mm on average.

*Texture and distribution*.—Smooth; discontinuous; basilar.

*Color* (*mature*).—2.5 GY 7/6 at 6 week age.

*Anthocyanin* (*mature*).—Absent.

*Color* (*immature*).—2.5 GY 6/8 at 1 week age.

*Anthocyanin* (*immature*).—Present, 10R 5/8.

Growing tips (young shoot):

*Pubescence*.—Absent; small number of wooly hairs (cobweb).

*Color*.—2.5 GY 6/8.

*Anthocyanin*.—Present, color very slight (10R 5/8).

*Shape*.—Wide open, straight.

*Apex*.—Normal, triangular, flat.

Leaves:

*Shape*.—Pentagonal.

*Apex*.—Pointed.

*Base*.—Rounded.

*Margin*.—Teeth irregular.

*Length of teeth on margin*.—1 to 8 mm.

*Shape of teeth on margin*.—Both sides convex.

*Texture* (*mature leaf*).—Upper surface: Smooth. Lower surface: Smooth, glabrous.

*Size*.—Immature, length: 8 cm at 10 days of age (average). Immature, width: 8 cm at 10 days of age. Mature, length: 13 cm at 20 days of age. Mature, width: 13 cm at 20 days of age.

*Color, immature leaf* (*4th leaf from growing tip*).—Upper surface: 2.5 GY 5/8. Lower surface: 2.5 GY 5/6.

*Color, mature leaf* (*9th leaf from growing tip*).—Upper surface: 5 GY 4/8. Lower surface: 5 GY 5/6.

*Venation*.—Pattern: Primary and secondary veins on the upper surface are visible (veins have lighter color than interveinal tissue); veins on lower leaf surface are raised. Color: Upper surface: 2.5 GY 6/10. Lower surface: 5 GY 8/8.

*Petiolar sinus*.—Half open.

*Petiole*.—Length: 5.7 cm. Diameter: 2 mm. Color: 5GY 7/6.

Floral cluster:

*General description and location*.—Small clusters, slender, some wings; Fruit located 3 to 5 nodes from base, mostly 4th node.

*Quantity of inflorescences per cluster*.—200 to 300 (high density).

*Size*.—Length: 14.5 cm on average, not including peduncle. Width: 7.2 cm on average, first two laterals spread.

*Peduncle length*.—5.2 cm on average.

*Peduncle width*.—7.2 mm; peduncle tapers with smallest width at the base.

*Inflorescences*.—Hermaphroditic.

*Stamens*.—Upright, Straight, 2 mm long.

*Anthers*.—Normal, cream color to yellowish brown.

*Date of bloom*.—Full bloom in mid-May; bloom duration=4 days.

*Pollen amount*.—Light to moderate, creamy yellow.

*Calyptra*.—5 segments; complete separation.

*Calyptra color*.—5GY 6/8.

Fruit:

*Time of year of commercial harvest and shipment*.—Late-July to mid-August.

*Cluster* (*primary bunches*).—General size: Medium, 575 grams. Length (without peduncle): 27.5 cm on average. Width: 16 cm on average. Density: Medium. Peduncle length: 6 cm on average. Peduncle diameter: 5.5 mm on average. Peduncle color: 5 GY 76. Number of berries per cluster: 150 on average. Berry: Size: Medium, 3 g. Shape: Globose. Uniformity: Very uniform. Brix content: 22.5° on Jul. 28, 2013. Size: Diameter: 18 mm on Jul. 28, 2013. Length: 18 mm. Skin color: Green Yellow (5GY 7/6). Pedicel: Length: 8 mm. Diameter: 1.5 mm. Color: 5GY 6/4. Strength of attachment to berry: Strong.

*Cluster* (*secondary bunches*).—General size: small/medium/large: Small. Length (without peduncle): 6 cm. Width: 4 cm. Density: Medium. Peduncle length: 11 cm. Peduncle diameter: 2.5 mm. Peduncle color: 5 GY 7/6. Number of berries per cluster: 10 on average. Berry: Size: Medium, 3 g. Shape: Globose. Uniformity: Fair. Brix content: 22° on Jul. 28, 2013. Diameter: 18 mm. Length: 18 mm. Skin color: 5GY 7/6. Pedicel: Length: 8 mm. Diameter: 1.5 mm. Color: 5 GY 6/4. Strength of attachment to berry: Strong.

Berry flesh:

*Color*.—Green (2.5 GY 8/4).

*Juice color*.—Clear.

*Juice production*.—Moderate.

*Thickness of skin*.—Thick.

*Flavor*.—Neutral.

*Fragrance*.—Neutral.

*Texture*.—Crisp.

*Seeds*.—'Seedless' with very small and soft seed rudiments that are not detectable when eating.

*Use*.—Fresh, table grape; raisins.

Disease and insect resistance: No particular resistance or susceptibility has been observed. Normal disease control practices can be used. Disease resistance is similar to Thompson Seedless.

What is claimed is:

1. A new and distinct grapevine plant as described and illustrated herein.

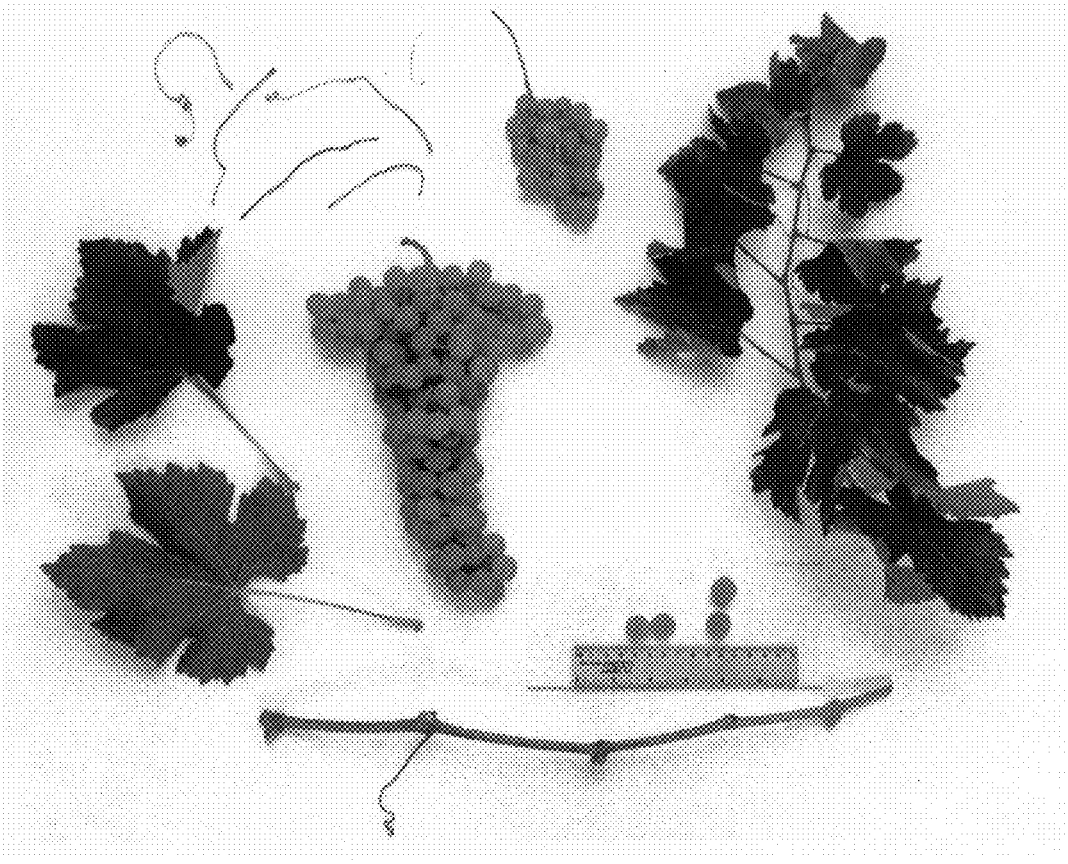

* * * * *